United States Patent [19]
Gustafsson

[11] Patent Number: 6,099,480
[45] Date of Patent: Aug. 8, 2000

[54] APPARATUS FOR MEASURING THE NO-GAS CONTENT OF A GAS MIXTURE

[75] Inventor: Lars Erik Gustafsson, Hässelby, Sweden

[73] Assignee: Aerocrine AB, Sweden

[21] Appl. No.: 09/125,872

[22] PCT Filed: Feb. 1, 1997

[86] PCT No.: PCT/SE97/00159

§ 371 Date: May 14, 1999

§ 102(e) Date: May 14, 1999

[87] PCT Pub. No.: WO97/32210

PCT Pub. Date: Sep. 4, 1997

[30] Foreign Application Priority Data

Feb. 26, 1996 [SE] Sweden .................................. 9600743

[51] Int. Cl.[7] ...................................................... A61B 5/08
[52] U.S. Cl. .......................................... 600/532; 73/23.3
[58] Field of Search .................... 600/532, 543, 600/538; 73/23.2, 23.3

[56] References Cited

U.S. PATENT DOCUMENTS

| | | | |
|---|---|---|---|
| 5,447,165 | 9/1995 | Gustafsson | 600/532 |
| 5,795,787 | 8/1998 | Silkoff et al. | 600/532 |
| 5,922,610 | 7/1999 | Alving et al. | 600/532 |

FOREIGN PATENT DOCUMENTS 0621051  10/1994  European Pat. Off. .

Primary Examiner—Cary O'Connor
Assistant Examiner—Navin Natnithithadha
Attorney, Agent, or Firm—Banner & Witcoff, Ltd.

[57] ABSTRACT

The present invention relates to apparatus for determining a relevant proportion (a) of a chosen gas, an NO-gas or $NO_2$-gas, present in a gas mixture (A), such as in a gas mixture deriving from the expiration air or inspiration air of a living being (1), wherein an adapted sample proportion of the breathing air is passed from an outlet (11) in the immediate vicinity of said being, via a hose (10') or the like, to measuring equipment (13') that includes a measuring chamber (14') that is placed under a subpressure and to which ozone gas is also supplied, wherewith the nitrogen oxide present reacts with the ozone-gas to form $NO_2$ and light, and wherein the apparatus includes a light measuring unit (13') which is adapted to evaluate the light thus generated and to calculate (18) the amount of predominant gas in the breathing air on the basis of this evaluation. The volume (14b') of the measuring chamber of such apparatus is adapted to include the volume enclosed in the hose (10') used. The hose-related valve (11a') or constriction that delimits the subpressure volume of the measuring chamber is provided in the close proximity of the being (1). A means (30) for reducing the water vapour in the breathing air sample (A), e.g. by cooling and/or freezing, is adapted upstream of the measuring chamber (14') to reduce or eliminate precipitation of water in the measuring chamber.

18 Claims, 2 Drawing Sheets

APPARATUS FOR MEASURING THE NO-GAS CONTENT OF A GAS MIXTURE

FIELD OF INVENTION

The present invention relates generally to apparatus for measuring the percentage of a chosen gas, a NO-gas or $NO_2$-gas, in a gas mixture.

The invention finds suitable application in evaluating the percentage of NO or $NO_2$ in the expiration air or inspiration air of a living being, preferably a human being.

More particularly, the invention relates to the type of apparatus in which a volume of expiration air or inspiration air suitable for test purposes is led to measuring equipment from an outlet in the immediate vicinity of said being, via a hose or like conduit.

In this application, the measuring equipment may include a measuring chamber which is placed under a sub-pressure and to which ozone gas ($O_3$) is delivered, wherewith the NO-content will react with the ozone gas to form $NO_2$ and light, and also a light-measuring unit adapted evaluate the number of photons or the like in the measuring chamber and to calculate in a calculating unit the predominating gas in the expiration air on the basis of said evaluation.

For the sake of simplicity, the following description will be made solely with reference to its application in respect of expiration air.

DESCRIPTION OF THE BACKGROUND ART

Several different designs of apparatus of the kind defined in the introduction are known to the art. Apparatus on which the present invention is based will be described summarily hereinafter with reference to FIGS. 1 and 2.

In this known construction, a chamber window that delimits the measuring chamber is comprised of a clear glass plate and the total chemiluminescence generated in the measuring chamber is measured.

It is also known, by way of an alternative, to incorporate a filter in the chamber window or to provide the window with a filter. The filter used in this respect is one that will extinguish light wave lengths shorter than 620 nm. Such a filter is used in $NO/NO_2$ analysis processes.

It is therewith known to deliver the gas mixture and the ozone gas continuously to the measuring equipment and particularly to the measuring chamber, through a respective hose-mounted throttle valve. Alternatively, the gas mixture can be delivered discontinuously, by controlling a number of valves in accordance with the expiration cycle.

The International Patent Publication WO 95/02181 (PCT/SE 94/00659) teaches a system of establishing the NO-content of the expiration air from a living being.

Since the present invention is based on the ability to evaluate relatively small amounts of nitrogen oxide (NO) present in a gas mixture, it can be mentioned that it is also known to evaluate the nitrogen oxide content of a gas with the aid of chemiluminescence, with the aid of, for instance, $NO/NO_2$-analyzers used by Monitor Labs, 8840, and marketed by Oleico AB, Lidingö, Sweden.

The presence of nitrogen oxide (NO) can also be shown by collection in distilled water to which iron (II) sulphate has been added, freeze-drying the mixture to dryness and thereafter shown as nitrite, either with the Diazo-reaction according to Martin, et al or with a Nitur-test qualitative nitrite stick.

Other known measuring instruments that operate with mass-spectrography can be used for this purpose.

A common feature of all earlier known methods of evaluating the NO-content of a gas mixture is that it is difficult to evaluate the time-wise short variation of the NO-content, for instance during a single expiration cycle.

SUMMARY OF THE PRESENT INVENTION

Technical Problems

When considering the earlier standpoint of techniques as described above, and as described in more detail hereinafter with reference to FIGS. 1 and 2, it will be seen that a technical problem resides in creating conditions that will enable the NO-content or $NO_2$-content of a gas mixture to be measured reliably in a measuring chamber, even in the case of very small NO- or $NO_2$-concentrations, without the gas to be measured adhering to the material of the sampling tube or channel to any appreciable extent.

It will also be seen that a technical problem resides in the ability to measure the time-wise variation of the NO-gas during an expiration cycle with satisfactory sensitivity Another technical problem is one of enabling a gas mixture to be delivered to a mixing volume formed in the measuring chamber with the aid of simple means, and to create upstream of this mixing volume conditions for a high gas mixture flow velocity.

Another technical problem is one of creating measuring conditions in the mixing volume that will enable sensitivity to be enhanced and the time-lags to be reduced, a requirement that is becoming more and more pronounced in respect of time-wise rapid changes in concentration.

A further technical problem is one of creating conditions with which the risk of interference from a delivered gas mixture can be reduced, particularly when measuring in a fluctuating system, such as in the case of inspiration and expiration cycles, and measuring the variation of the NO-content of the expiration air during an expiration cycle.

A further technical problem is one of creating conditions which will enable the uncertainties of the measuring result that originate from temperature differences and/or water vapour contents of the gas mixture (expiration air) to be reduced or preferably eliminated.

With respect, in particular, to measuring expiration air that is saturated with water vapour and which has a temperature of 35–40° C., a technical problem resides in the ability of measuring the NO-content of the gas in a colder atmosphere without precipitating water in the measuring chamber.

Thus, a technical problem resides in mastering those problems that are concerned with diverting a part of expiration air that is saturated with water vapour to a subpressurized space with subsequent precipitation of water and thereafter leading said part of the gas to the measuring chamber, in which a measuring window is cooled by the cooling system of a measuring tube with subsequent precipitation of water on the window.

A further technical problem is one of reducing the exposure of the NO-part of the gas and the mixture of this part with precipitated water in the measuring system, such exposure and mixing having a detrimental affect on the measuring result in the measuring chamber.

A technical problem also resides in the creation of conditions that will enable precipitated water to be removed with a minimum dead volume, via cooling or freezing-out moisture from the gas mixture in the expiration air.

A further technical problem is one of creating conditions whereby the NO-content of a gas mixture can be evaluated quickly and repeatedly with a slight delay, and to realize the measures that are required to achieve a reduced dead volume.

In this regard, a technical problem is one of creating with the aid of simple means conditions that will shorten considerably the time taken to transfer the aforesaid gas-part between the expiration air outlet and the measuring chamber used but nevertheless provide a large physical distance therebetween with a small volume.

A technical problem resides in realizing those advantages that are afforded when the path from the subpressure volume of the measuring chamber to a valve or constriction that delimits the subpressure volume of the measuring chamber, which valve or constriction is located very close to the expiration air outlet, is "stretched out" via a narrow hose.

Another technical problem is to realize in respect of such measures the conditions that shall be created in order to reduce or totally prevent the formation of condensation on the chamber window or the like in a simple manner when the photon-delivering measuring tube is cooled.

Another technical problem is one of realizing the importance of and the advantages associated with allowing the subpressure volume of the measuring chamber to be adapted to include the whole of the enclosed volume of the hose or channel that extends between a measuring chamber of the measuring equipment and the expiration air outlet, by delimiting the subpressure volume of the measuring chamber with a narrow hose and with a hose-related valve or constriction located in the close proximity of the expiration air and said being.

Another technical problem is one of realizing the significance of and the advantages afforded by providing means for reducing the water vapour content of the water-vapour saturated part of the expiration air, e.g. by cooling and/or freezing, and to provide said means upstream of the measuring chamber so as to enable conditions to be created for an adapted reduction or elimination of water precipitation in the measuring chamber and along the hose, and particularly on the cold chamber window.

A further technical problem is one of realizing the significance of giving the hose a volume that is adapted in relation to the volume of the measuring chamber.

Another technical problem is one of realizing the significance of giving the hose a volume that is adapted to the volume of the measuring chamber and that is dimensioned for a rate of flow wherein only a small amount of nitrogen oxide or no nitrogen oxide at all will fasten to the inner walls of the hose used or dissolve in freely precipitated water.

Still another technical problem is one of realizing the significance of choosing a long and narrow hose which is active under subpressure in order to reduce the time-lag caused by the length of the hose and the volume thereof, among other things.

Yet another technical problem is one of realizing the significance of reducing the amount of water vapour present to an extent such as to reduce or inhibit the risk of interference in the measuring chamber from gas mixture delivered thereto, particularly when the expiration air sample is delivered periodically.

Another technical problem is one of realizing the significance of forming the hose from two mutually parallel hoses with end-related valves so as to enable the expiration air sample to be passed alternately through one hose or the other.

Another technical problem is one of providing for the aforesaid purpose a measuring chamber where the chamber window can be eliminated, by allowing the light-measuring unit to be coupled light-wise directly to the measuring chamber, wherein the light-measuring unit forms and constitutes the chamber window that would otherwise be used.

Solution

With the intention of solving one or more of the above technical problems, the present invention takes as its starting point apparatus which will enable a relevant proportion of a chosen gas, a NO-gas or $NO_2$-gas present in a gas mixture, to be measured, such as in the gas mixture deriving from the expiration air of a living being, wherein an adapted sample proportion of the expiration air is passed from an outlet in the immediate vicinity of said being, via a hose or the like, to measuring equipment that includes a measuring chamber that is placed under a subpressure and to which ozone gas is also continuously supplied, wherewith the nitrogen oxide present reacts with the ozone-gas to form $NO_2$ and light, and wherein the apparatus includes a light measuring unit which is adapted to evaluate the light thus generated, and a calculating unit which calculates the amount of predominant gas in the expiration air on the basis of this evaluation.

With the intention of solving one or more of the aforesaid technical problems, it is proposed in accordance with the invention that the subpressure volume of the measuring chamber of such apparatus is adapted to include the volume enclosed in the hose used, that a hose-related valve or constriction that delimits the subpressure volume of the measuring chamber is provided in the close proximity of said being, and that reduction of the water vapour in said expiration air sample, e.g. by cooling and/or freezing, is adapted upstream of the measuring chamber to reduce or eliminate precipitation of water on the measuring window of the measuring chamber, among other things.

In accordance with proposed embodiments that lie within the scope of the inventive concept, it is proposed in accordance with the invention that the hose shall be given a volume that is adapted in relation to the volume of the measuring chamber.

It is also proposed that the hose is given a small volume in relation to the measuring chamber and is dimensioned for a rate of flow at which only a small amount of nitrogen oxide gas or no nitrogen oxide gas will be able to adhere to the inner surfaces of the hose used.

It is also proposed that the hose is given a short length so as to reduce the time-lag that is occasioned by hose length. Alternatively, the hose can be given a small internal cross-sectional area.

It is also proposed in accordance with the invention that the water vapour is reduced to an extent that will also reduce, or inhibit, the risk of interference in the measuring chamber from gas mixture delivered thereto, particularly when the expiration air sample is delivered periodically and in step with the expiration cycle.

It is particularly proposed in accordance with the invention that the hose comprises two mutually parallel hoses having end-related valves which function to switch the expiration air sample from one hose to the other.

According to one embodiment of the invention, the light meter is connected light-wise directly to the measuring chamber, so as to obviate the need for the earlier used chamber window.

It is also proposed in accordance with the invention that the subpressure in the subpressure volume of the measuring chamber is below 0.3 atm (atmospheres), preferably below 0.02 atm.

Advantages

Those advantages primarily afforded by the inventive apparatus reside in the provision of conditions which not only enable the concentration of a relevant sample of gas, such as a NO-gas, in a gas mixture deriving from expiration air or inspiration air of a living being to be evaluated quickly, but also to enable the moisture content of the expiration gas to be removed to an extent at which no water will be precipitated in the measuring chamber, despite a predominant subpressure in said chamber and a lower temperature in relation to the water-vapour saturated expiration air.

The main characteristic features of an inventive apparatus are set forth in the characterizing clause of the accompanying claim 1.

BRIEF DESCRIPTION OF THE DRAWINGS

An earlier known apparatus for measuring a relevant, selected gas sample, an NO-gas sample, in a gas mixture originating from the expiration air of a living being, and apparatus constructed in accordance with the present invention will now be described in more detail with reference to the accompanying drawing, in which.

DESCRIPTION OF THE KNOWN TECHNIQUE

Figure 1:
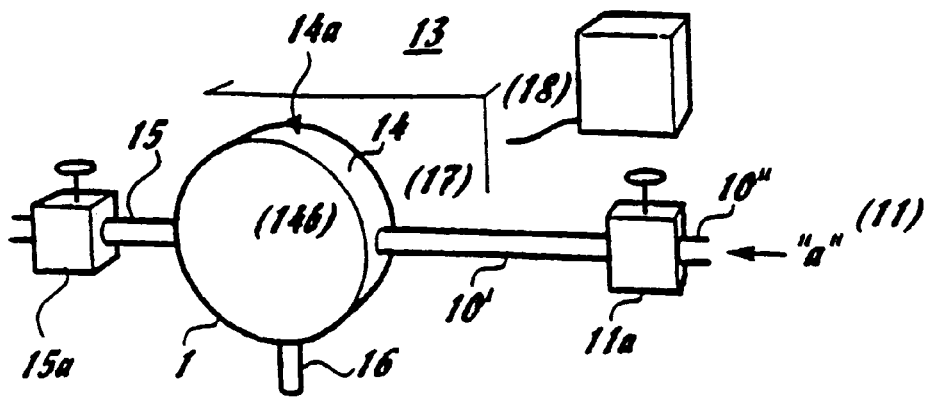
FIG. 1 illustrates the principles of an earlier known measuring apparatus that includes a measuring chamber.

FIG. 1 thus illustrates an earlier known apparatus for measuring a relative percentage sample (a) of a chosen gas, a NO-gas or $NO_2$-gas, in a gas mixture (A). It is assumed that the gas mixture (A) derives from the expiration air of a living being.

It is thus known to pass a sample (a) of expiration air (A) through a hose 10" or the like from an outlet 11 in the immediate vicinity of said being to measuring equipment 13 that includes a measuring chamber 14 that is placed under subpressure and to which ozone-gas ($O_3$) is also passed continuously through a pipe or hose 15.

When the valve 11a is actuated to deliver the ozone-gas ($O_3$) and the gas mixture including the nitrogen oxide sample (NO) to the measuring chamber 14, the nitrogen oxide present will react with the ozone gas as they come into contact in the measuring chamber 14 such as to form $NO_2$ and light, said measuring chamber 14 having an enclosed volume 14b which is placed under a subpressure via a pipe 16.

When the measuring process is discontinuous, the adjustable valve 11a can be used. In the case of a continuous measuring process, or a discontinuous measuring process in respect of a continuously flowing gas mixture and ozone-gas, the valves (11a, 15a) can be replaced with constrictions. Only the valve alternative is described in the exemplifying embodiments.

A light-measuring unit 17 and a calculating unit 18 connected thereto are adapted to evaluate the light generated on the one hand and to calculate the predominating NO-gas-content present in the expiration air (A) on the other hand.

With regard to the known technique, the valve 11a shown in FIG. 1 is placed very close to the measuring chamber 14 and the hose section 10' is very short so as to limit the volume 14b of the measuring chamber 14.

The subpressure volume 14b of the interior of the measuring chamber 14 has therewith been concentrated to solely the volume of the measuring chamber 14, since the additional volume represented by one or more short hose sections can be disregarded.

However, the hose section 10" has been given a long length in practice, when this section shall place the measuring chamber 14 in communication with the expiration air "A" close to the mouth and nose of the living being, a human being.

The hose has been given a relatively large cross-sectional area, because of the resistance to flow created by the hose interior.

Figure 2:
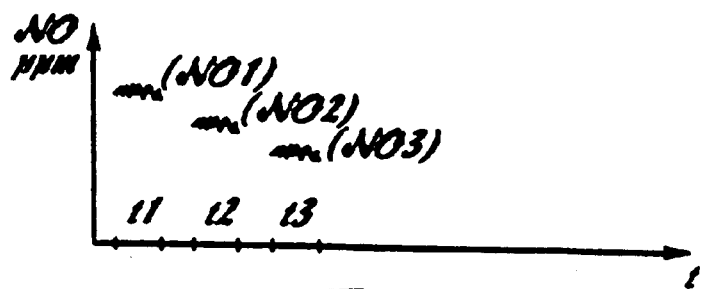
FIG. 2 illustrates the variation of the NO-content in time in respect of a measuring apparatus according to FIG. 1, with clearly decreasing values of the percentage of nitrogen oxide in the expiration air.

FIG. 2 shows the result obtained when measuring the nitrogen oxide content of a gas mixture taken from the expiration air (A) that is saturated with water vapour when using apparatus of the kind illustrated in FIG. 1 and with a well-adapted hose section length 10".

FIG. 2 illustrates the NO-fraction of expiration air (A) in the measuring equipment 13 with a constant NO-content.

The NO-gas content ($NO_1$) evaluated during the time period t1 can be considered to represent the true constant value.

However, it is evident from FIG. 2 that the NO-content of the gas mixture will decrease time-wise with each expiration cycle. Thus, the NO-content (NO2) of the gas mixture during the time period (t2) is lower than the NO-content during the preceding time period and higher than the NO-content (NO3) during the following time period (t3).

It is believed that this change indicated in the measuring result is because the NO-gas tends to be absorbed by the water vapour present in the expiration air. This water vapour does not only precipitate in the hose 10', and primarily the hose 10", but also precipitates in the measuring chamber 14. Such precipitation is caused by the decrease in temperature that occurs in the measuring chamber 14 among other things, and also as a result of the vapour coming into contact with the cold chamber window 14a.

This clear decrease in the NO-content of the gas mixture shown in the measuring result may also be due to adhesion of NO-gas on the inner surfaces of the hose 10", 10' when the hose is made of a plastic material, and then particularly in those parts (10") that are placed under atmospheric pressure.

The aim of the invention is to eliminate, or at least reduce, this source of measuring error, such that the measuring results (NO1, NO2, NO3) will have the same values at mutually the same concentrations.

DETAILED DESCRIPTION OF PREFERRED EMBODIMENTS

Figure 3:
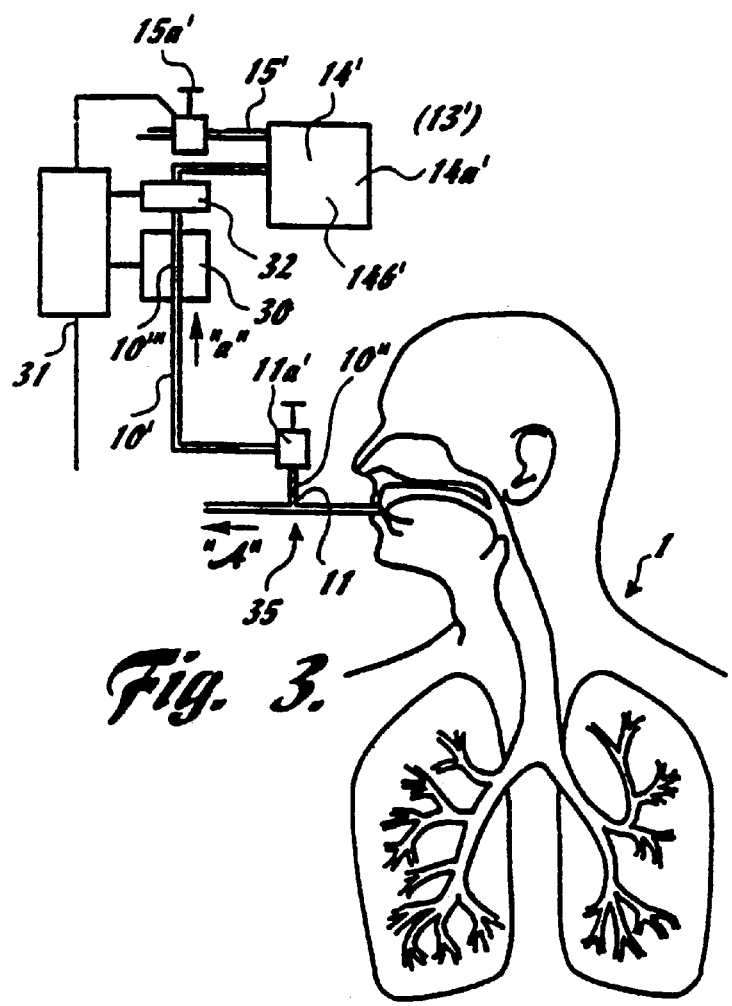
FIG. 3 illustrates the principle of an inventive apparatus.

In the embodiment of the invention illustrated in FIG. 3, the measuring equipment 13' and the subpressure volume 14b' of the measuring chamber 14' are adapted to include the enclosed volume of the hose section 10' used, with the aid of a hose-related valve 11a' (or constriction) which limits the subpressure volume of the measuring chamber and which is disposed in the close proximity of the human being 1 and close to the expiration air (A).

Because at least the hose section 10' shall be able to withstand a subpressure, etc., that corresponds to the subpressure in the measuring chamber, certain deliberations are necessary.

A small hose cross-sectional area would result in a high rate of flow with respect to the sample of expiration air "a" to be measured. A small hose cross-sectional area decreases the timelag and enhances sensitivity. A small hose cross-sectional area withstands a greater subpressure. A small hose cross-sectional area also affords a greater cooling effect. A small hose cross-sectional area also reduces the subpressure volume of the measuring chamber.

When seen against this background, it will be evident that the hose section preferably will be short and have a small cross-sectional area, although not too short and not too small. A hose cross-section having a diameter of 1.0–10 mm, preferably 1.5–2.0 mm, is considered suitable in this regard.

In the case of shorter hose sections, the hose may have a smaller diameter, such as a diameter of 0.5–5.0 mm.

The length of the hose section 10' will at least be sufficient to enable means (30) for reducing the water vapour content of the sample quantity (a) of expiration air (A), such as by cooling and/or freezing, to be placed in the hose section 10'.

The means 30 is placed upstream of the measuring chamber 14' and is intended to reduce or eliminate precipitation of water in the measuring chamber 14' and on the cold chamber window 14a'.

The means 30 will preferably be placed close to the valve 11a' and will function to freeze away the water that is released as a result of the hose subpressure in relation to the pressure of the expiration air (A). At least a further quantity of water shall be frozen away, so as to prevent the precipitation of water on the measuring window (14a') in the measuring chamber 14'.

The means 30 may simply comprise placing a hose section 10''' in a coolant mixture having a temperature of −5° C. or lower.

The volume enclosed in the hose within said section 10''' can be written as "π·r²·l", where "l" is the length of the section 10''', whereas the inner cooling surface can be written as "π·2r·l".

It follows from this that the ratio volume/cooling surface area will be r/2, wherewith a narrow hose cross-section (10''') is preferred in this respect.

However, the hose section 10' will have a small volume in relation to the internal volume of the measuring chamber 14', and will be dimensioned in other respects to withstand external pressure loads.

The hose section 10' is also given a small volume in relation to the internal volume of the measuring chamber 14' and is dimensioned for a rate of flow at which only a small quantity of nitrogen oxide or no nitrogen oxide at all will be able to adhere to the inner walls of the hose section chosen.

The hose section 10' will preferably have a short length so as to reduce the time-lag caused in the measuring result by the length of hose used. In practice, it has been found that a hose length of up to 12 meters at a subpressure of 0.02 atm results in a time-lag of about 1 sec. and a response time of 0.3–0.4 sec. to reach 90% of the amplitude of a square increase in the NO-content.

The means 30 will conveniently be controllable so as to enable the extent to which water vapour is removed to be adjusted, and will be sufficiently large to reduce or inhibit the risk of interference in the measuring chamber 14' from the gas mixture delivered thereto.

It will be particularly observed that the sample (a) taken from the expiration air (A) may be delivered periodically. To this end, there is used a control unit 31 which coacts with the cooling unit, or the means 30, and also with a flow meter 32.

The control unit 31 will also be adapted to control a valve 11a' coacting with the measuring chamber 14'. As before mentioned, the valves may be replaced with constrictions.

Figure 4:
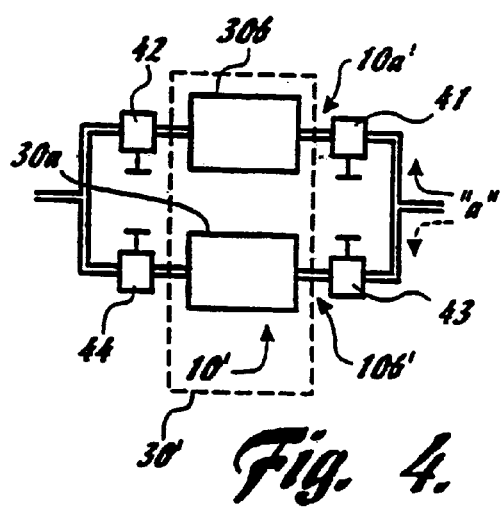
FIG. 4 illustrates an alternative embodiment of the invention.

As evident from FIG. 4, the hose section 10' may conveniently have the form of two parallel hoses 10a', 10b' with end-related valves 41–44 for switching the sample (a) of expiration air (A) alternately from one hose 10a' to the other hose 10b'.

Each hose part herewith includes a cooling unit 30a, 30b. This enables the cooling unit 30a to be switched to a defrosting mode when the hose section 10a' is not used to transport the sample (a) of expiration air, and the cooling unit 30b to be switched to a defrosting mode when the hose section 10a' is in use.

In order to achieve this, it is necessary for the control unit 31 to control the valves 41, 42 and 43, 44 respectively to their closed and open positions.

The parallel hose parts 10a', 10b' may alternatively be coordinated with one cooling unit 30' and defrost the hose sections by heating an electric conductor placed in said hose section and removing the melt water.

When the illustrated apparatus is required to determine the $NO_2$-content of the expiration air, a known converter 35 for converting $NO_2$ to NO may be placed upstream of the valve 11a'.

Such a $NO_2$ to NO converting unit 35 utilizes atmospheric pressure and a temperature of about 300° C. in a molybdenum converter.

The rates of flow will preferably be adapted so that the gas volume is changed in the measuring chamber 14' from three to ten times per second and in respect of the hose 10' about ten times per second.

It will be understood that the invention is not restricted to the aforedescribed and illustrated exemplifying embodiments thereof and that modifications can be made within the inventive concept as illustrated in the following claims.

What is claimed is:

1. Apparatus for determining a NO content of expired air, said apparatus comprising: a measuring chamber being held at subpressure, at least one conduit having an inlet for positioning proximate a patient, said at least one conduit being arranged for conducting a sample taken from a flow of air expired by the patient to the measuring chamber, and a device for regulating the sample flow, said device for regulating the sample flow being situated in close proximity of said inlet.

2. Apparatus according to claim 1, wherein said device includes a constriction of said at least one conduit, said constriction being situated in close proximity of the inlet.

3. Apparatus according to claim 1, wherein said device includes a valve, said valve being situated in close proximity of the inlet.

4. Apparatus according to any one of claims 1–3, wherein said at least one conduit includes two mutually parallel conduits, each said conduit including a valve for switching the expiration air sample from one conduit to the other conduit.

5. Apparatus according to claim 1, wherein a volume of the measuring chamber and a volume enclosed in the at least one conduit are held under subpressure.

6. Apparatus according to claim 1, wherein the volume enclosed in the at least one conduit is less than the volume of the measuring chamber.

7. Apparatus according to claim 1, wherein the at least one conduit has a diameter in the interval of 0.5 to 10 mm.

8. Apparatus according to claim 1, further comprising means for cooling and/or freezing the at least one conduit, said means for cooling and/or freezing being arranged upstream of the measuring chamber to reduce or eliminate precipitation of water in the measuring chamber.

9. Apparatus according to claim 1, wherein the measuring chamber comprises a chemiluminescence device.

10. Apparatus according to claim 5, wherein the pressure in the measuring chamber volume and the at least one conduit volume is below 0.3 atm.

11. Apparatus according to claim 1, wherein the expired air sample is delivered periodically to the measuring chamber.

12. Apparatus according to claim 1, wherein the expired air sample is delivered continuously to the measuring chamber.

13. Apparatus according to claim 1, wherein a measuring unit is connected light-wise directly to the measuring chamber.

14. Apparatus according to claim 7, wherein the diameter of the at least one conduit is in the interval of 1.0 to 5.0 mm.

15. Apparatus according to claim 14, wherein the diameter of the at least one conduit is in the interval of 1.5 to 2.0 mm.

16. Apparatus according to claim 10, wherein said pressure is below 0.2 atm.

17. Apparatus according to claim 1, wherein said at least one conduit includes at least one channel or at least one hose.

18. Apparatus according to claim 7, further comprising means for cooling and/or freezing the at least one conduit, said means for cooling and/or freezing being arranged upstream of the measuring chamber to reduce or eliminate precipitation of water in the measuring chamber.

* * * * *